United States Patent [19]
Hui et al.

[11] Patent Number: 5,919,576
[45] Date of Patent: Jul. 6, 1999

[54] IMMOBILIZED BIOLOGICAL MEMBRANES

[75] Inventors: Sek Wen Hui, Williamsville, N.Y.;
Anne Plant, Arlington, Va.;
Madhusudhana Rao, Hyderabad, India

[73] Assignees: Health Research Inc., Buffalo, N.Y.;
Government of the USA, Nat'l Institute of Standards, Washington, D.C.

[21] Appl. No.: 08/975,842

[22] Filed: Nov. 21, 1997

[51] Int. Cl.[6] .............................. B22F 3/26; B32B 15/00; B21D 39/00

[52] U.S. Cl. .................... 428/545; 428/594; 428/615; 428/623; 428/624; 428/936; 428/938; 427/2.1

[58] Field of Search ..................................... 428/545, 594, 428/615, 621, 622, 623, 624, 936, 938; 427/2.1

[56] References Cited

U.S. PATENT DOCUMENTS 5,728,590  3/1998  Powell ..................................... 436/547

OTHER PUBLICATIONS

Plant, Gueguetchkeri and Yap, "Supported Phospholipid/Alkanethiol Biomimetic Membranes: Insulating Properties", Biophysical Journal, 1994, vol. 67, pp. 1126–1133.

*Primary Examiner*—Nathan M. Nutter
*Attorney, Agent, or Firm*—Hodgson, Russ, Andrews, Woods & Goodyear, LLP

[57] ABSTRACT

A composition comprising an immobilized biological membrane is provided. The functional immobilized biological membrane consists of a support structure, a metal layered onto a surface of the support structure, an alkanethiol monolayer assembled onto the metal, and a biological membrane deposited on the alkanethiol monolayer. Also provided is a method of producing the immobilized biological membrane, wherein the method involves contacting an alkanethiol with a metal surface of a support structure in forming an alkanethiol monolayer assembled onto the metal, and depositing a biological membrane onto the alkanethiol monolayer such that the biological membrane becomes associated with the alkanethiol monolayer. Uses of the biological membrane include as a sensing indicator in a biosensor, as an adsorbent in a chromatography system, and as a coating for medical devices.

18 Claims, 7 Drawing Sheets

IMMOBILIZED BIOLOGICAL MEMBRANES

This invention was made with government support under grant GM 30969 awarded by the National Institutes of Health. The government has certain rights in the invention.

FIELD OF THE INVENTION

This invention relates to novel compositions comprising supported biological membranes, and methods for making the supported biological membranes. More particularly, the present invention relates to the immobilization of a biological membrane onto a surface in a manner that preserves structure, and function (e.g., molecular interactions such as receptor binding and signaling) of the biological membrane.

BACKGROUND OF THE INVENTION

Artificial biological membranes have been used for a variety of applications including for medical and industrial applications. Artificial membranes are known to those skilled in the art, and include a mixture of collagen and elastin (U.S. Pat. No. 5,416,074), an amphiphilic compound (e.g., a phospholipid or other purified membrane constituent; U.S. Pat. No. 4,931,498), or supported phospholipid/alkanethiol bilayers ("supported hybrid bilayer membranes") comprising a phospholipid monolayer formed onto a alkanethiol monolayer. Regarding the latter, it has been described previously that when alkanethiols are applied to a thin film of gold, a self-assembled monolayer of alkanethiol is formed by adsorption of the alkanethiols to the surface of the gold (see, e.g., Nuzzo et al., 1987, *J. Am. Chem. Soc.,* 109:2358–68; Prime and Whiteside, 1991, *Science,* 252:1164–67). Such self-assembled monolayers have been used as a surface onto which fibronectin is adsorbed in forming a tissue culture substrate (Mrksich et al., 1996, *Proc. Natl. Acad. Sci. USA,* 93:10775–8); and as a tetracyanoquinodimethane mediated biosensor for glucose (Pandey et al., 1995, *Biosens. Bioelectron.,* 10:669–74).

Biological (cell) membranes, as they exist in nature, differ from artificial membranes in several respects. For example, cell membranes have active transport systems for macromolecules including cations, proteins, and DNA; whereas lipid bilayers alone lack such transport systems. Additionally, typical artificial membranes comprise phospholipid-molecules only; whereas biological membranes include an ordered architecture of phospholipids, and membrane-associated proteins such as enzymes and receptor molecules. While a lipid bilayer can be formed by the addition of phospholipid vesicles to alkanethiol monolayer on gold, at the time of the invention it was not believed that this method could be applied to cell membranes. This is because lipid vesicle spreading and advancement over the alkanethiol monolayer requires the surface of the monolayer to be attractive to the vesicles, thereby promoting the hydrophobic interaction between the alkyl chains of the alkanethiols and the phospholipid molecules. However, the architecture and multi-component composition of biological membranes present steric hindrances to the interaction necessary for phospholipid vesicles to spread and advance over, and immobilize to, the alkanethiol monolayers. Such steric hindrances are repulsive and destabilizing forces thought to help oppose the attractive interaction between phospholipids and alkanethiol monolayer, and thereby would preclude the formation of a stable association, and resultant immobilization, between phospholipids and an alkanethiol monolayer on gold. Moreover, biological membranes typically comprise a multitude of proteins with extramembrane domains (e.g., protein segments protruding from the portion of the membrane that faces the cell cytoplasm, and protein segments exposed to the portion of the cell membrane that faces extracellularly). However, a multitude of proteins has not been observed to be adsorbed onto alkanethiol monolayers (Prime and Whitesides, 1991, supra). It has also been demonstrated that the phospholipid/alkanethiol bilayer shows little nonspecific adsorption of protein, and thus prevents the adsorption of proteins onto either the alkanethiol monolayer or the metal film of the support (Plant et al., 1995, *Anal. Biochem.* 226:342–348). Further, the close association between the thiol sulfur and gold of the alkanethiol monolayer may preclude the normal insertion of a transmembrane protein (Plant et al., 1994, *Biophys. J.* 67:1126–33).

Additionally, membrane-associated proteins represent sensing and recognition molecules residing in biological membranes. It is appreciated by those skilled in the art that such membrane-associated proteins lose their specificity or activity (e.g. enzymatic activity) upon slight alterations of their lipid environment (e.g., membrane depolarization) and/or upon alterations in the membrane's ordered architecture (see, e.g., Brenner et al., 1977, *Can. J. Biochem.* 55:126–33; Reifarth et al., 1997, *J. Membr. Biol.* 155:95–104). For example, free fatty acids, and related compounds such as aliphatic aldehydes, have been shown to inhibit cell membrane-associated enzymatic activity by perturbing the lipid bilayer and disturbing protein-membrane lipid interactions of cell membranes (Lapshina et al., 1995, *Scand. J. Clin. Lab. Invest.* 55:391–7). Therefore, any attempt to immobilize a biological membrane could potentially affect the activity inherent to components of the membrane in its natural setting.

Thus, because natural biological (cell) membranes differ from artificial membranes, and to date only artificial membranes have been immobilized, there remains a need for methods to immobilize biological membranes. Such a method would obviate the current and tedious approach of isolating membrane proteins, and attempting to reconstitute lipid bilayers with such isolated proteins.

SUMMARY OF THE INVENTION

It is therefore an object of the invention to provide novel compositions comprising immobilized (supported) biological membranes.

It is a further object of the present invention to provide novel compositions comprising immobilized biological membranes which retain at least a portion of the membrane function or activity as observed for the biological membrane in its natural setting (e.g., as part of a living cell).

Yet another object of the invention is to provide methods for immobilizing biological membranes to a surface.

Another object of the invention is to provide methods for immobilizing biological membranes to a surface thereby resulting in immobilized biological membranes which retain at least a portion of the membrane function or activity as observed for the biological membrane in its natural setting (e.g., as part of a living cell).

These and further features and advantages of the invention will be better understood from the description of the preferred embodiments when considered in relation to the figures in which:

DETAILED DESCRIPTION OF THE PREFERRED EMBODIMENTS

Definitions

The term "adsorbent" is used herein, for purposes of the specification and claims, to mean the use of an immobilized biological membrane according to the present invention to bind to one or more components in human body fluids, wherein the components include, but are not limited to, antibodies, antigens, cytokines, and immune effector cells.

The term "alkanethiol" is used herein, for purposes of the specification and claims, to an aliphatic thiol substrate which, in a monolayer form, functions to enable self assembly of a biological membrane onto the substrate surface in forming an immobilized biological membrane according to the present invention. Such aliphatic thiols may comprise thioalkanes including, but not limited to unsubstituted alkanethiols, for example, decanethiol, hexadecanethiol, octadecanethiol, and a combination thereof; or alpha-substituted or omega-substituted alkanethiols which may have one or more hydroxy, alkoxy, carboxy or alkoxycarbononyl substitutents, or a combination thereof; and a combination thereof. In particular, for certain applications it may be desirable to use a mixture of alkanethiols in producing a self-assembled monolayer onto which the biological membrane is to be deposited.

The term "biological membrane" is used herein, for purposes of the specification and claims, to mean cell membranes including, but not limited to, extracellular or outer cell membranes, and intracellular or organelle cell membranes.

The term "biosensor" is used herein, for purposes of the specification and claims, to mean the use of an immobilized biological membrane according to the present invention in an information processing system. The biological membrane is immobilized onto the sensor surface allowing for one or more binding partners of the membrane to interact by specific binding with a mobile reactant. Upon the molecular interaction with (e.g., binding between) the reactant and binding partner, a signal is sent, thereby allowing for qualitative and quantitative characterization of such molecular interaction. A "portion of natural membrane function or activity" means that the immobilized biological membrane retains some or all of the same function or activity demonstrated by the natural membrane (e.g., as part of a cell) such that the molecular interaction between the reactant and binding partner can take place on the immobilized biological membrane, and can be characterized either qualitatively or quantitatively. Cell membranes typically may contain membrane components including, but not limited to, receptors and enzymes, which are cell type-specific and/or function-specific. For example, the cell membrane of human omental lipocytes possesses stereospecific D-glucose-uptake activity and specific insulin-binding activity (Brenner et al., 1977, supra). Thus, it will be appreciated by those skilled in the art that a certain type of cell membrane may be desired for forming the immobilized biological membrane of the biosensor, depending on the nature of the reactant desired to be characterized. Additionally, the biological membrane may be chosen for biocompatibility.

The term "metal" is used herein, for purposes of the specification and claims, to mean a metal which interacts with a reactive group (e.g., sulfur) of the alkanethiol such that a stable, self-assembled monolayer structure of alkanethiol forms. Such metals include, but are not limited to gold, mercury, silver, platinum, and combinations (amalgams) thereof. The thickness of the layer of metal will vary depending on the desired use of the final product. Thus, while gold films of a thickness ranging from 50 angstroms (Å) to about 2000 Å are described herein, other thicknesses (e.g., <50 Å or over 2000 Å) may be employed. A metal either comprises the support structure, or is layered onto a support structure in forming a metal surface.

The terms "immobilized" or "supported" are used herein, for purposes of the specification and claims, to mean adsorption, coating or bonding the biological membrane according to the present invention to a support surface or structure via an association with an alkanethiol monolayer self assembled onto a metal layer. The support surface or structure can include, but is not limited to a sensor or information processing chip; a particulate material to be coated and used for chromatographic separations; and an implantable medical device, or implantable prosthetic device, or implantable graft.

It is demonstrated herein that, unexpectedly, alkanethiol self-assembled monolayers formed on a metal, can stably associate with biological membranes in a similar fashion as the spontaneous fusion between phospholipid vesicles and alkanethiol self-assembled monolayers. More particularly, a single layer of cell membrane becomes stably associated with the alkanethiol monolayer, thereby forming an immobilized biological membrane as confirmed by analyses including morphological observations, measurement of membrane thickness, increase in wettability of the surface, and decrease in the capacitance. Additionally, at least some enzymatic activity of the biological membrane was observed for the immobilized biological membrane, suggesting that the supported biological membrane retains at least a portion of the natural membrane activity and function.

In the following embodiments used to illustrate the invention, it is important to consider the following concept. The use of erythrocyte membranes has been validated and widely accepted by those skilled in the art as a model representative of cell membranes in general. For example, erythrocyte membranes have been used as a model for cell membrane component function (e.g., receptors; Boyer et al., 1996, *Mol. Pharmacol.* 50:1323–9) and activity (e.g., enzymatic; Currie et al., 1997, *Curr. Biol.* 7:184–90); for the study of age-associated changes in cell membranes (Glaser et al., 1994, *Proc. Natl. Acad. Sci. USA,* 91:7879–83); the effects of drugs, such as muscle relaxants (Mizuguchi et al., 1994, *Anesth. Analg.* 78:1077–81) or glutathione (Lenzi et al., 1994, *Hum. Reprod.* 9:2044–50), on cell membranes; for cell membrane structural interactions (Smith and Bormann, 1995, *Proc. Natl. Acad. Sci. USA,* 92:488–91); and for assessing free radical-induced damage (Hajela et al., 1997, *FEBS Lett.* 406:255–8) and the prevention thereof by antioxidants (Chan and Tang, 1996, *J. Pineal Res.* 20:187–91; Oya et al., 1997, *Biosci. Biotechnol. Biochem.* 61:263–6).

EXAMPLE 1

This example illustrates substrate preparation for the methods and compositions according to the present invention. The initial substrate preparation involves the deposition of a metal onto a surface of a support structure. The support structure provides a framework for the methods and compositions according to the present invention, and the chemical nature of such structure will depend on the desired use of the final product (e.g., including, but not limited to, a sensor or information processing chip; a particulate material to be coated and used for chromatographic separations; and an implantable medical device including, but not limited to, an implantable prosthetic device, or implantable graft). Thus, the support structure may be fabricated from materials which supply the structural integrity and other properties required for the desired use of the immobilized biological membrane. As the specific character of the material of the support structure does not in and of itself constitute the subject matter of the present invention, it should be apparent to those skilled in the art that a wide latitude of choice can be exercised in selecting a material suitable as a support structure onto which is formed an immobilized biological membrane. For example, it is known to those skilled in the art that materials such as gold can be deposited on and bonded to a number of materials including glass, metal electrodes, ceramics, composite resins, porcelain, and elastic fibers (see, e.g., Hansson and Moberg et al., 1993, *Scand. J. Dent. Res.* 101:243–51; Palmer and Bale, 1987, *Histochemistry* 88:91–5).

In the case where a metal surface is desired to be added to a support surface, a first step is to deposit a metal onto the support surface such that a stable association is formed between the two. To illustrate this first step, gold film was affixed to a number of surfaces. Gold was evaporated onto glass as follows. The glass is cleaned by placing the glass in a saturated solution of potassium dichromate for several hours, then washed in distilled water and ethanol. Chromium was deposited onto glass by evaporation in a vacuum. Using a similar technique, gold was evaporated onto the chromium layer of the glass. In one embodiment, gold was deposited at a thickness of approximately 500 Å.

For conductance purposes, gold may be deposited on a metal coated surface. For example, in constructing a biosensor for glucose, gold was sputter deposited onto chromium-coated silicon wafers to a thickness of 200 nanometers (nm) (Pandey et al., 1995, supra). Also, commercially available sensor chips comprise a thin layer (approximately 450 Å) of gold deposited on borosilicate glass (Plant et al., 1995, supra). In constructing an electrode, for example, gold may be sputtered over a 300 Å titanium layer on borosilicate glass. The gold electrodes may then be cleaned using three cycles of treatment with a warm potassium dichromate solution, followed by rinsing with 3% hydrofluoric acid (Plant et al., 1994, supra). In this exemplary electrode, the gold film may consist of a layer approximately 1000 Å thick.

The next step in producing an immobilized biological membrane is to form a self-assembled monolayer of alkanethiol on the metal. In that regard, the procedure may vary depending on the particular alkanethiol used to form the monolayer. For example, freshly prepared gold-filmed supports, or freshly cleaned gold-filmed supports, were placed into a solution of alkanethiol (1 mM) in absolute ethanol for at least 12 hours. The resulting alkanethiol monolayer-coated substrates were then rinsed extensively with ethanol, dried under nitrogen, and then used for its desired purpose. The strong interaction between gold and the thiol sulfur of the alkanethiol causes the spontaneous formation of a well-ordered and complete alkanethiol monolayer on the gold film of the support. The formation of the alkanethiol monolayer can be confirmed by advancing contact angle and electrical impedance measurements using methods known in the art. For example, the formation of an octadecanethiol monolayer on a gold surface was assessed by measuring the contact angle. The contact angle measured for water on this hybrid surface was 105° C., an indication of extremely poor wettability which is consistent with the formation of a layer of alkane chains (e.g., an alkanethiol monolayer). The electrical impedance of the insulating alkane layer may also be measured. For example, sensor chips covered with a well-ordered octadecanethiol monolayer have a specific capacitance of $0.94\,\mu F/cm^2$ (Plant et al., 1995, supra). As another example, a decanethiol monolayer assembled onto a freshly cleaned gold electrode was characterized by a capacitance of approximately $1.60\,\mu F/cm^2$ (Pandey et al., 1995, supra).

EXAMPLE 2

This example illustrates preparation of isolated cell membranes which can be used to produce an immobilized biological membrane according to the present invention. Prior to preparing immobilized biological membranes according to the present invention, cell membranes are isolated from the cell type of interest. There are a variety of methods known to those skilled in the art for the isolation of cell surface membranes, intracellular membranes, or fragments thereof, that involve homogenization or cell disruption, followed by differential and isopycnic centrifugation; or purification by affinity chromatography (as reviewed by Scott, 1976, *Science,* 194:743–5; and *Methods in Enzymology,* Vol. 31, Parts A & B, eds. Fletcher and Packer, 1974, Academic Press). Some specific examples are as follows. For cells that can be cultured in vitro, cell surface vesiculation can be induced by incubation of the monolayer cultures with 250 mM formaldehyde in calcium-magnesium phosphate buffered saline (Scott, 1976, supra). In general, formaldehyde (25 to 250 mM) or N-ethylmaleimide (1 to 10 mM) are effective in inducing vesicle formation. The vesicles may then be collected, and sedimented by centrifugation at 30,000 g for 30 minutes at 4° C. Cell membrane fragments prepared in this way contain components characteristic of plasma membranes including all the major classes of phospholipids, sphingomyelin, cholesterol, and membrane proteins.

Cell membranes can be isolated from tissue by homogenizing 10 g of tissue in 100 ml of 0.32 M sucrose, 5 mM Tris-HCl, pH 7.0 at 4° C. with 10 strokes of a homogenizer at 800 rpm. The homogenate is then centrifuged at 1000×g for 10 minutes, and the resulting supernatant is centrifuged at 17000×g for 1 hour. The resulting membrane pellet may be further purified by discontinuous sucrose density centrifugation.

Erythrocyte membrane complex (representative of membrane vesicles) can be isolated from erythrocytes collected from the blood of healthy donors using any one of several methods known to those skilled in the art. In one method for preparing an erythrocyte membrane complex by osmotic lysis, potassium rich physiologic salt solution ("rPBS", 3 mM NaCl, 150 mM KCl, 5 mM NaPi, pH 7.4) can be used to wash erythrocytes. A 0.1 ml volume of rPBS containing $10^{10}$/ml erythrocytes is placed in a dialysis bag (molecular size cutoff of 12000–14000 Kd), and then immersed in a 500 ml of diluted rPBS (⅙ rPBS) for 0.5 hours at 4° C. Another incubation for 0.5 hours in 500 ml PBS at 25° C. is performed to reseal the osmotic pores on the erythrocyte membranes. The resealed erythrocyte membrane complex was washed several times in PBS, and in a balanced salt solution. An alternative procedure was utilized to prepare erythrocyte membrane complex for the following embodiments illustrating the formation of immobilized biological membranes according to the present invention. More particularly, rabbit or human erythrocytes were washed three times in a buffer containing 5 mM sodium phosphate and 150 mM sodium chloride (PBS) in which the buffy coat is removed in the initial washes. Washed erythrocytes were then lysed in precooled 5 mM phosphate buffer, pH 8.0 by mixing at a ratio of 1:20, and the lysate was centrifuged at 20,000×g for 10 minutes. The translucent and whitish membrane pellets (erythrocyte membrane complex) were pooled and washed three times in 5 mM phosphate buffer, pH 8.0.

EXAMPLE 3

This example illustrates preparation of hybrid membrane layers in producing an immobilized biological membrane according to the present invention. More particularly, this example illustrates the deposition of cell membranes onto an alkanethiol monolayer, wherein the alkanethiol monolayer is formed onto the metal of a support structure. It will be recognized that various modifications exist for the method of preparing the immobilized biological membranes according to the present invention.

In one embodiment, alkanethiol monolayer coated substrates were formed by depositing either octadecanethiol or decanethiol onto freshly prepared gold film on a glass support. The alkanethiol monolayer-coated substrates were placed in a petri dish, and then covered with a suspension of cell membranes (erythrocyte membrane complex). After an overnight incubation at 4° C., the substrate samples were rinsed thoroughly with water by repeated dilution and removal of most of the fluid, while keeping the substrate samples moist. After the final rinse, the water was removed from the dish, leaving only a thin film of liquid on the substrate samples. At this point, the samples were allowed to air dry.

Contact angle measurements allowed assessment of the changes in wettability of the resulting surface. A freshly evaporated gold surface is hydrophilic, as represented by a contact angle of approximately 25°±5°. After a self assembled monolayer of alkanethiol forms on freshly evaporated gold film, the surface becomes hydrophobic, with a contact angle of 90°±10°. However, the addition of a biological membrane to the alkanethiol monolayer alters the hydrophobic surface to one of more polar character, as evidenced by the lowering of the contact angle to 40°±5°. The change in the hydrophobic surface to one of more polar character is one indication that the biological membrane has associated with the alkanethiol monolayer to form an immobilized biological membrane.

Figure 1:
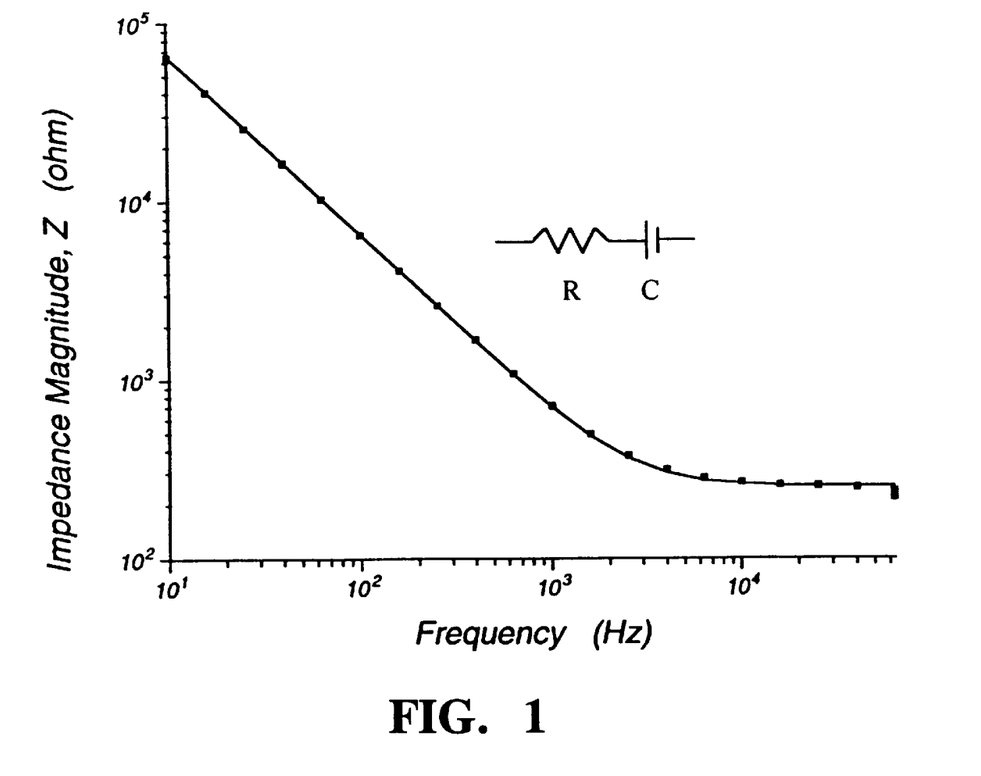
FIG. 1 is a graph illustrating impedance plotted versus frequency for the immobilized biological membrane.

To estimate the thickness of the resulting surface, ellipsometric measurements were taken at an incident angle of 70° on dried substrate samples through the different stages of treatment. Optical thickness measurements by ellipsometry on dry substrate samples containing a decanethiol monolayer or octa-decanethiol monolayer were 12.5 Å and 16 Å, respectively. After treatment with the biological membrane preparation, the resulting surface was approximately 40 Å thicker than the support with the alkanethiol monolayer. Frequency dependent impedance response was used as an in situ method of estimating the thickness of alkanethiol monolayer-coated substrates and the surfaces of alkanethiol monolayer-coated substrates treated with the cell membranes. Briefly, the gold film served as the bottom of the electrochemical cell and as the working electrode with an exposed area of 0.32 $cm_2$. The reference electrode was silver/silver chloride, and a platinum wire served as an auxiliary electrode. The cell membrane preparation comprised erythrocyte membrane complex suspended in 20 mM Tris, 150 mM NaCl, 0.1% thimerosal, pH 7.4. The cell membranes were added directly to the electrochemical cell, and the association between the cell membranes and the alkanethiol monolayer was allowed to occur in situ. Impedance measurements were made in the presence or absence of the cell membranes. Removal of the cell membrane suspension and rinsing of the electrochemical cell were performed without disrupting the surface of the electrode. Impedance measurements were made at a dc potential of 0 volts (V) and a sinusoidal ac potential of +/–10 mV. Capacitance values were determined by impedance measurements in buffer (20 mM Tris, 150 mM NaCl, 0.1% thimerosal, pH 7.4). The capacitance of the dielectric layer (e.g., alkanethiol monolayer/cell membrane bilayer hybrid) that covers the electrode can be determined by the magnitude of the impedance response as a function of frequency. The capacitance, C is calculated by the formula:

$$Z = R + \frac{1}{j\omega C}$$

wherein Z is the impedance magnitude, $\omega=2\pi f$, f=frequency of the applied ac potential, $j=\sqrt{-1}$, and R is the resistance. As illustrated in FIG. 1, the supported biological membrane demonstrated an impedance response similar to that observed for a simple circuit model consisting of a resistor (the electrolyte solution) in series with a capacitor (the alkanethiol monolayer/cell membrane bilayer hybrid).

Table 1 compares the capacitance ($C_m$ in $\mu F/cm^2$) of supported membranes including an alkanethiol monolayer (Table 1, "monolayer"), an alkanethiol monolayer/lipid bilayer (palmitoyl, oleoyl-phosphatidylcholine) hybrid (Table 1, "monolayer/lipid bilayer hybrid"), and an alkanethiol monolayer/biological membrane bilayer (erythrocyte membrane complex) hybrid (Table 1, "monolayer/membrane hybrid"). The capacitance for the lipid bilayer or the erythrocyte membrane layer is calculated from the capacitance of the respective hybrid and the capacitance of the alkanethiol monolayer, as illustrated in the following formula:

TABLE 1

$$\frac{1}{C_{m,bilayer}} = \frac{1}{C_{m,hybrid}} - \frac{1}{C_{m,monolayer}}$$

| | octadecanethiol | decanethiol |
|---|---|---|
| monolayer | 1.01 | 1.47 |
| monolayer/lipid bilayer hybrid | .68 | .96 |

TABLE 1-continued $$\frac{1}{C_{m,bilayer}} = \frac{1}{C_{m,hybrid}} - \frac{1}{C_{m,monolayer}}$$

|  | octadecanethiol | decanethiol |
|---|---|---|
| lipid bilayer (calculated) | 2.1 | 2.0 |
| monolayer/membrane hybrid | 76 | 1.36 |
| membrane layer (calculated) | 3.2 | * |

*large increase in capacitance indicating that the short chains of the decanethiol monolayer may be perturbed by the addition of biological membranes such that the monolayers are no longer the barrier to current that they were before the addition of the biological membrane.

Capacitance ($C_m$) is inversely proportional to the thickness (d) of the dielectric bilayer, as illustrated in the formula:

$$C_m = \kappa\epsilon_0/d$$

where $C_m$ is the specific capacitance (normalized for electrode area), $\kappa$ is the dielectric constant of the layer, and $\epsilon_0$ is the permittivity of the free space ($8.85 \times 10^{-8}$ $\mu$F/cm). Assuming a dielectric constant for the alkanethiol of 2.25, the thickness of the self-assembled alkanethiol monolayer is approximately 20 Å. The thickness of the insulating region (i.e., the acyl chain region) of the lipid bilayer is expected to be approximately 13 Å, based on X-ray crystallography studies of similar lipids (Lewis and Engelman, 1983, *J. Mol. Biol.* 166:211–17). Using a dielectric constant of 2.7 (Plant et al., 1994, supra), the thickness calculated for the lipid bilayer is approximately 11 Å. The capacitance of the biological membrane is larger than that demonstrated by the lipid bilayer, and thus the calculated thickness of the supported biological monolayer (approximately 7.5 Å) is less than the thickness of the supported lipid bilayer. However, it is noted that optical thickness measurements by ellipsometry approximate the supported biological membrane to be 40 Å thick. There are one or more possible reasons for the discrepancy between the two measurement techniques. One likely possibility is that the dielectric constant is larger for biological membranes than lipid bilayers because, for example, biological membranes are more complex in structure and contain additional components (e.g., proteins) as compared to pure lipid bilayers. Thus, increasing the dielectric constant to a value larger than that assumed in the above referenced calculations would result in a larger calculated thickness of the supported biological membrane.

EXAMPLE 4

This example illustrates another embodiment of the preparation of hybrid membrane layers in producing an immobilized biological membrane according to the present invention. This example also illustrates the deposition of cell membranes onto an alkanethiol monolayer, wherein the alkanethiol monolayer is formed onto the metal of a support structure. It will be recognized that various modifications exist for this embodiment of preparing the immobilized biological membranes according to the present invention.

In this embodiment, alkanethiol monolayer-coated substrates were formed by depositing octadecanethiol onto freshly prepared gold film on a glass support. The alkanethiol monolayer-coated substrates were floated face down in cell membranes (erythrocyte membrane complex) suspended in buffer so that the alkanethiol monolayer was in direct contact with the biological membranes. After an overnight incubation at 4° C., the substrate samples were rinsed thoroughly with water by repeated dilution and removal of most of the fluid, while keeping the substrate samples moist. After removing most of the final rinse, the substrates were removed from the dish, and the substrate surfaces were allowed to air dry.

In this embodiment, the immobilized biological membrane was analyzed for the extent of coverage on the support surface by environmental scanning electron microscopy. Using this method at 4° C. and a pressure of 5.6 torr caused water to condense on the immobilized biological membrane. Flat areas of wetting were observed on the immobilized biological membrane, as distinguished from the large, round droplets that form on alkanethiol monolayers observed under similar conditions. This is consistent with the more hydrophilic and polar nature of the biological membrane as compared to the hydrophobic alkanethiol monolayer. Importantly, the wetting pattern observed appears to be uniform over the entire coated surface of the support, indicating that the immobilized biological membrane uniformly covers the treated surface (e.g., over an area spanning over hundreds of $\mu m^2$).

EXAMPLE 5

This example illustrates another embodiment of the preparation of hybrid membrane layers in producing an immobilized biological membrane according to the present invention. This example also illustrates the deposition of cell membranes onto an alkanethiol monolayer, wherein the alkanethiol monolayer is formed onto the metal of a support structure. It will be recognized that various modifications of this embodiment exist for preparing the immobilized biological membranes according to the present invention.

In this embodiment, alkanethiol monolayer coated substrates were formed as follows. A thin layer of carbon was evaporated onto cleaved mica. A thin film of gold was then deposited on the carbon layer, and then octadecanethiol was deposited onto the freshly prepared gold film. A drop of the biological cell membrane suspension (e.g., erythrocyte membrane complex suspended in buffer) was placed in the center of, and in contact with, the self-assembled alkanethiol monolayer without completely covering the entire surface area. After an overnight incubation at room temperature, the area of the surface which was in contact with the biological membrane suspension was carefully rinsed with several washes of water. The substrate samples were then allowed to air dry. The area containing the supported biological membrane was then shadowed with platinum at an angle of 29° C. from the plane of the surface for analysis by transmission electron microscopy; or the area was gold sputtered for analysis by scanning electron microscopy. The sputtered films were then floated on water and transferred onto grids for electron microscopy.

Transmission electron microscopy was used to provide a closer analysis of the morphology and uniformity of the immobilized biological membrane. The images resulting from transmission electron microscopy showed the area containing the immobilized biological membrane was darker and less homogenous in texture when compared to surrounding area of alkanethiol monolayer alone. More particularly, the area containing the immobilized biological membrane was rougher in texture, and few small, unfused membrane vesicles were observed. In contrast, the surrounding area of alkanethiol monolayer alone (not exposed to the membrane complex) was flat and featureless. That a boundary around the area of biological membrane deposition could be observed is an additional indication of the added thickness to the substrate which is attributable to the supported biological membrane.

Scanning electron microscopy was also used to provide a closer analysis of the morphology and uniformity of the immobilized biological membrane. The images resulting from scanning electron microscopy also showed the area containing the immobilized biological membrane as darker and less homogenous in texture when compared to surrounding area of alkanethiol monolayer alone. However, the exact thickness of the supported biological membrane could not be determined by this technique due to the unknown thickness of the gold sputtering coating. More particularly, the area containing the immobilized biological membranes did not exhibit visible holes, nor any evidence of individual membrane vesicles adhering to the treated surface. Thus, the images by scanning electron microscopy also indicate that the deposited biological membrane is uniformly spread in extended sheets on the alkanethiol monolayer. This is an unexpected result, since it was believed that the architecture and multi-component composition of biological membranes would preclude the formation of a stable association, and resultant immobilization, between phospholipids and an alkanethiol monolayer, as described in more detail herein.

EXAMPLE 6

This example illustrates another embodiment of the preparation of hybrid membrane layers in producing an immobilized biological membrane according to the present invention. This example also illustrates the deposition of cell membranes onto an alkanethiol monolayer, wherein the alkanethiol monolayer is formed onto the metal of a support structure. It will be recognized that various modifications of this embodiment exist for preparing the immobilized biological membranes according to the present invention.

In this embodiment, a suspension of biological membranes (erythrocyte membrane complex) were contacted to the alkanethiol monolayer-coated substrates by either self assembly or by Langmuir-Blodgett transfer. Self assembly is described in the previous examples, and is characterized by vesicle spreading of the deposited biological membrane over the surface of the alkanethiol monolayer-coated support, wherein portions of the spread membrane are immobilized to the alkanethiol monolayer via hydrophobic interactions between the membrane and the monolayer. For Langmuir-Blodgett transfer, the biological membrane (e.g., erythrocyte membrane complex) suspension was spread along an air-water interface by allowing the membrane suspension to drip down a rod and onto the surface of a Langmuir trough. The surface pressure was maintained below 10 dyne/cm. A substrate containing the alkanethiol monolayer was then dipped vertically (either at a 90 degree angle, or at a smaller angle) to the surface through the interface from the air and into the water. The immobilized biological cell membrane (membrane-coated substrate) was kept submerged under water for all subsequent operations for analysis by atomic force microscopy. The substrate sample was placed under the liquid scanner of an atomic force microscope such that a layer of buffered solution was retained between the scanner and the sample. Images were obtained at room temperature using a silicon nitride tip on a cantilever with a spring constant of 0.032N/m. The typical force applied to the sample was 10 nN, and forces up to 30 nN were applied. The images obtained by atomic force microscopy showed that the deposit of immobilized biological membrane appeared to be uniform, with a roughness of approximately 1.4 nm. Like the images by other electron microscopy techniques described herein, by atomic force microscopy there was evidence for extensive coverage of the deposited biological membrane onto the substrate surface.

To ensure that the material seen on the deposited area is material comprising the biological membrane and not substrate alone, the force applied to the scanning tip was increased stepwise from 9 nN to 30 nN (e.g., 9 nN, 16 nN, 22 nN, and 30 nN) in order to perturb loosely adhering material. Also, increasing the force applied to the deposit area allowed approximation of the depth of the deposited material as well as the strength of association (adherence) between the deposited material and the underlying substrate. At a force of 30 nN, the height of the scanned deposit area is approximately 5.7 nm below the deposited surface. This measured thickness of the deposited material is similar to the total thickness of 4 nm as measured by ellipsometry for the dry complex of immobilized biological membrane (alkanethiol monolayer/erythrocyte membrane complex hybrid).

EXAMPLE 7

This example illustrates another embodiment of the preparation of hybrid membrane layers in producing an immobilized biological membrane according to the present invention. This example also illustrates the deposition of cell membranes onto an alkanethiol monolayer, wherein the alkanethiol monolayer is formed onto the metal of a support structure. It will be recognized that various modifications of this embodiment exist for preparing the immobilized biological membranes according to the present invention.

Figure 2:
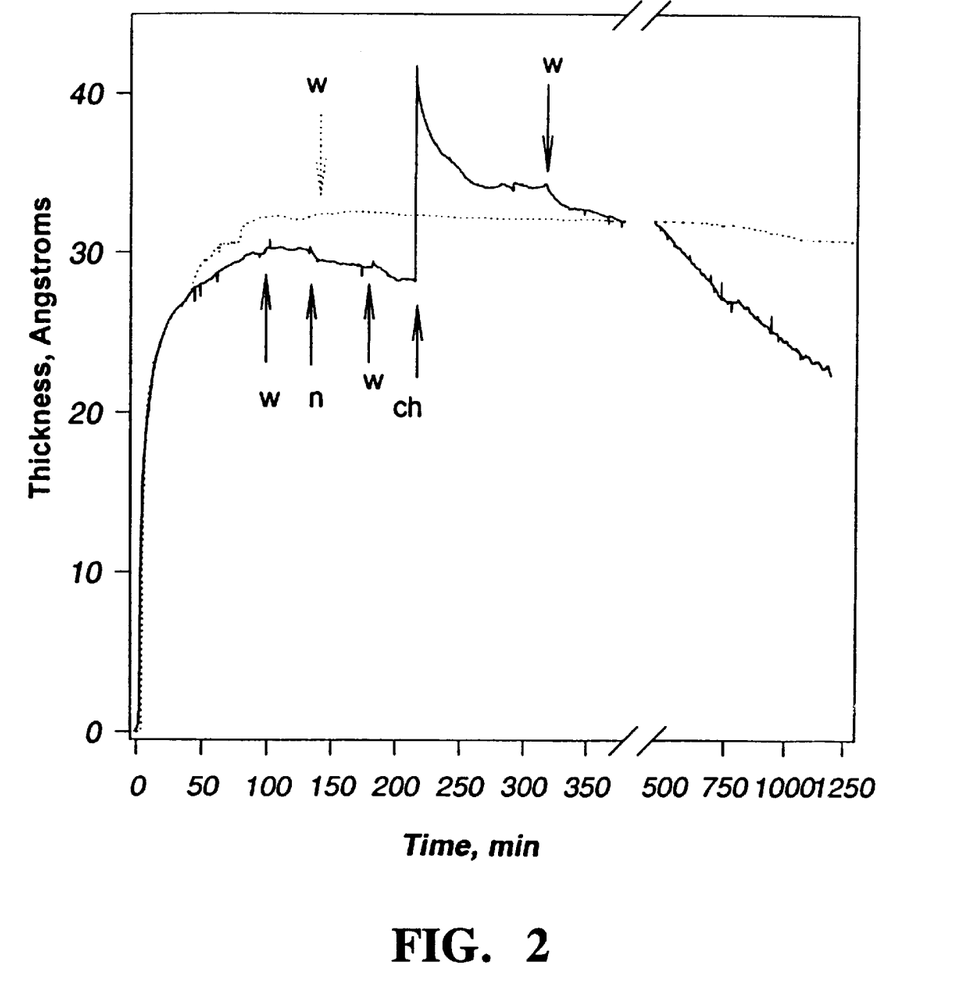
FIG. 2 is a graph illustrating the kinetics and nature of the association between an alkanethiol monolayer and a biological membrane.

In this embodiment, the biological membrane was deposited onto the alkanethiol monolayer in a flow cell environment for purposes of allowing analysis by surface plasmon resonance. Surface plasmon resonance analysis was used to provide information regarding the kinetics and the chemical association of the interaction between biological membrane and the alkanethiol monolayer when forming an immobilized biological membrane according to the present invention. The device used for this analysis comprises an optical measuring unit, a flow cell (volume of 30 $\mu$l) into which the alkanethiol monolayer-coated substrate is mounted, and a peristaltic pump. All operations and data accumulation were controlled with a computer and customized software, and additional calibrations have been described previously (Silin et al., 1997, *J. Coll. Inter. Sci.* in press). A semiconductor laser provided p-polarized light at 750 nm. The delay time between measurements was 10 seconds, and the sensitivity of the device was ±0.06 Å for layers with a refractive index of 1.45. Calibration was performed with solutions of different concentrations of glycerol in water. Erythrocyte membrane complex suspensions, at a concentration of approximately 1 mg/ml total protein, was pumped at a rate of 50 $\mu$l/minute through the flow cell containing the alkanethiol monolayer-coated substrate mounted therein. The change in the angle of the surface plasmon line minimum, which is indicative of an increase in thickness of the surface layer and corresponds to the association between the deposited membrane and the alkanethiol monolayer-coated substrate, was monitored in real time. Since surface plasmon resonance is sensitive to changes in refractive index at a metal surface, the buffer composition and temperature were kept constant throughout the analyses to minimize the differences in the refractive index. In FIG. 2 is illustrated the kinetics of the biological membrane complex with the substrate surface. More particularly, the association of the erythrocyte membrane complex with an octadecanethiol monolayer-coated substrate reaches a steady-state in less than two hours under continuous flow conditions. By this technique, the apparent increase in thickness due to the addition of the biological membrane complex is approximately 30 Å. In similar conditions, and when a decanethiol monolayer-coated substrate was used, the increase in thickness is approximately 27 Å. Additionally, even when the concentration of the biological membrane complex to be deposited was varied (e.g., between 0.2 mg and 1 mg total protein/ml), the increase in thickness due to the addition of the biological membrane complex was measured to be 30±3 Å.

Alternatively, surface plasmon resonance may be used with the immobilized biological membrane according to the present invention in a flow cell environment in forming a biosensor. The biosensor comprises an optical measuring unit, a flow cell having a surface onto which is immobilized the biological membrane, and a peristaltic pump. The biosensor may further comprise a information processing means to control all operations, and data accumulation. In that regard, surface plasmon resonance (or other techniques by which thickness can be measured; e.g. capacitance measurements, ellipsometry, atomic force microscopy) may be used to detect in a sample, placed in contact with the flow cell, a change in thickness due to the molecular interaction (e.g., binding between) a reactant present in the sample, and its specific binding partner comprising a component of the deposited biological membrane, thereby allowing for qualitative and quantitative characterization of such molecular interaction. More particularly, the thickness of the immobilized membrane as measured before the sample is contacted with the immobilized biological membrane, is compared to the thickness of the immobilized biological membrane upon or after contact with the sample. A change in the thickness, as observed from this comparison and which represents a specific interaction between the reactant present in the sample and the immobilized biological membrane, may either be an increase or decrease in thickness. For example, an increase in thickness may occur when the reactant specifically binds, and remains bound, to the immobilized membrane. A decrease in thickness may result, for example, when the reactant has specific enzymatic (e.g., proteolytic) activity for a component on the surface of the immobilized biological membrane, thereby causing cleavage of the component from the biological membrane.

In terms of the nature of the association, extensive (overnight) flowing of buffer solution over the immobilized biological membrane did not remove the deposited biological membrane, as illustrated in FIG. 2 (FIG. 2, dotted line). To determine if carbohydrates played a significant role in the chemical association between the deposited biological membrane and the alkanethiol monolayer and the formation the immobilized biological membrane according to the present invention, the alkanethiol monolayer/erythrocyte membrane complex hybrid was treated in situ with neuraminidase. Treatment with neuraminidase was expected to cause selective removal of N-acetylneuraminic acid. It is appreciated by those skilled in the art that N-acetylneuraminic acid is an abundant carbohydrate in membrane glycolipids and glycoproteins in cells from a spectrum of stages of differentiation and tissue origins. As shown in FIG. 2 (↑ labelled with "n"), the addition of neuraminidase at a concentration of 1 unit/ml resulted in an apparent decrease in the thickness due to cleavage of surface carbohydrate groups. Rinsing with buffer resulted in a further decrease in thickness, presumably removing weakly bound cleaved or partially cleaved N-acetylneuraminic acid, and/or loosely bound neuraminidase, from the surface. The result was a significant net decrease in the thickness of the hybrid layer of about 2 Å. In that regard, it is noted that polysaccharides account for approximately 8% by dry weight of the composition of the erythrocyte membrane complex, and that N-acetylneuraminic acid constitutes approximately 20% of the total polysaccharides. With that in mind, the observation of a reduction in thickness of 2 Å after neuraminidase treatment reasonably correlates with removal of N-acetylneuraminic acid from the erythrocyte membrane complex.

To continue the analysis of the nature of the association between the deposited biological membrane and the alkanethiol monolayer, and subsequent to the neuraminidase treatment, the immobilized biological membrane was treated with chymotrypsin. This was expected to cleave certain peptide bonds. The addition of chymotrypsin resulted in an initial dramatic increase in the apparent thickness of the immobilized biological membrane, presumably due to the enzyme's high affinity binding to the membrane surface (FIG. 2; ↑ labelled with "ch"). Then over time, a reduction in the thickness of the hybrid layer was observed. The net change in thickness of the hybrid layer due to the activity of chymotrypsin was approximately 6 Å, which confirms that: (a) a substantial amount of protein is associated with the hybrid layer; and (b) membrane proteins appear to play a significant role in the chemical association between the deposited biological membrane and the alkanethiol monolayer, and the formation the immobilized biological membrane according to the present invention.

In summary, both carbohydrate moieties and proteins of the biological membrane complex appear to play a significant role in the chemical association between the deposited biological membrane and the alkanethiol monolayer, and the formation the immobilized biological membrane according to the present invention. It is also important to note that the in the enzyme cleavage analyses described in this embodiment, the data was corrected for the changes in the refractive index of the respective solution due to the high concentration of protein enzyme added to the solution.

EXAMPLE 8

This example illustrates that the immobilized biological membrane according to the present invention is functional. As pointed out previously, membrane-associated proteins represent sensing and recognition molecules residing in biological membranes; and that such membrane-associated proteins can lose their specificity or activity (e.g. enzymatic activity) upon slight alterations of their lipid environment (e.g., membrane depolarization) and/or upon alterations in the membrane's ordered architecture. Therefore, any attempt to immobilize a biological membrane could potentially affect the activity inherent to components of the membrane in its natural setting. However, to be a particularly useful biological supported membrane, some specific biological activity of the biological membrane should be retained.

To assess whether the methods of the present invention for producing an immobilized biological membrane also resulted in an immobilized biological membrane retaining some biological function, the activity of a membrane associated protein was measured. More specifically, and in continuing with the illustration of using an erythrocyte membrane complex as the biological membrane deposited onto an alkanethiol monolayer-coated substrate, the activity of acetylcholine esterase (ACTHase) was measured. ACTHase, an enzyme marker for erythrocytes, is associated with the outer leaflet of erythrocyte membranes and hydrolyzes the substrates acetylcholine and acetylbetamethylcholine. In this analysis, the alkanethiol monolayer (either decanethiol or octadecanethiol)-coated substrates were carefully floated on a suspension of erythrocyte membrane complexes overnight at 4° C. to allow for self assembly of the immobilized biological membrane. Unabsorbed membrane material was removed, and the substrate surface was rinsed thoroughly with buffer (PBS). During rinsing, the substrate surface was kept submerged in the buffer, and was not allowed to pass through the air/water interface. For measuring the ACTHase activity, the buffered solution covering the substrate samples was replaced by a solution of acetylcholine chloride (12.5 mM) in buffer. The formation of the product (thiocholine), formed as a result of cleavage by ACTHase, was detected after 30 minutes by mixing an aliquot of the solution (obtained from above the sample substrate) with Ellman's reagent (10 mM) at room temperature, and measuring the optical absorbance at 410 nm (see, e.g., Steck and Kant, 1974, *Meth. Enzymol.* 31: 172–80). ACTHase activity, associated with the immobilized biological membrane, was assayed over a period of several days.

Figure 3:
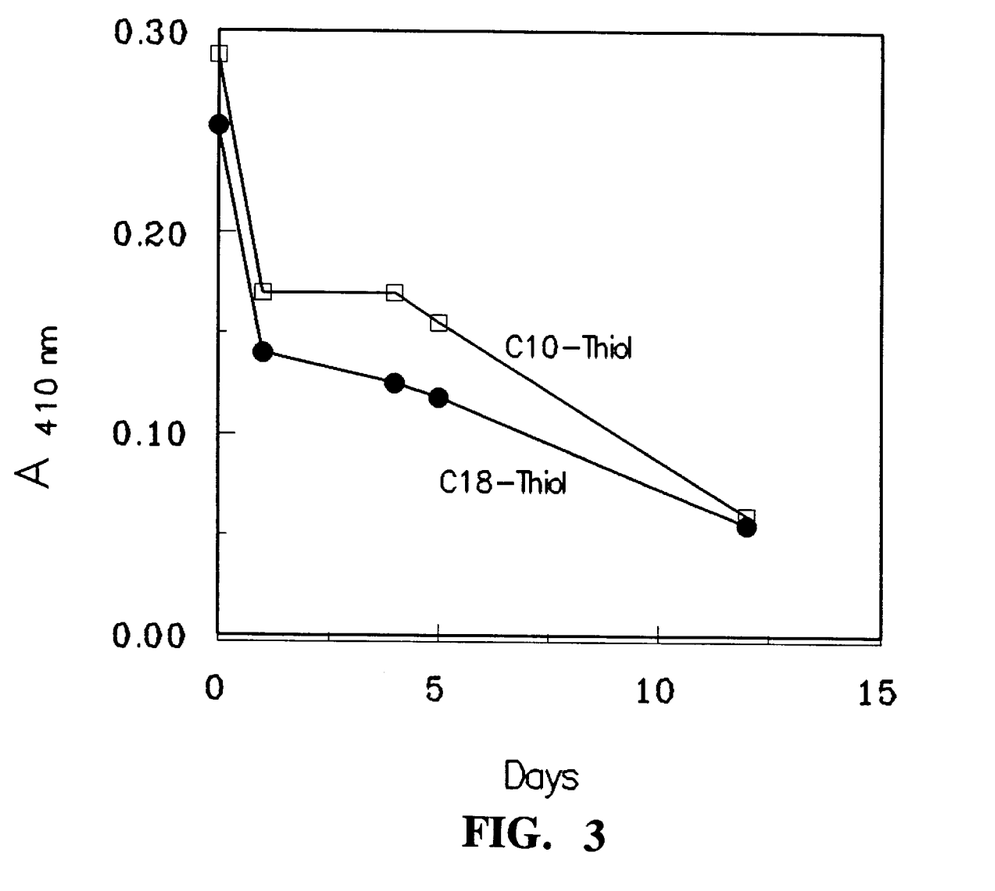
FIG. 3 is a graph illustrating an ACTHase activity profile associated with biological membranes immobilized on decanethiol (-□-) or on octadecanethiol (-●-).

Illustrated in FIG. 3 is the ACTHase activity associated with the immobilized biological membrane, over a period of several days, and after extensive washing and careful handling. The graphs in FIG. 3 reflect a series of measurements (and an activity profile of averaged from several experiments), wherein each measurement was from a surface area of 2.6 cm$^2$. As shown for biological membranes immobilized on decanethiol (FIG. 3, -□-), and for biological membranes immobilized on octadecanethiol (FIG. 3, -●-), the associated ACTHase activity was initially high, declined to a moderate but significant level up until about day 5, and then declined rapidly after day 5. FIG. 3 clearly illustrates that the ACTHase activity associated with the outer leaflet of the erythrocyte membrane complex is clearly retained after the erythrocyte membrane complex is immobilized onto an alkanethiol monolayer-coated substrate. This is an unexpected result; i.e., despite immobilization of the erythrocyte membrane complex, biological function of the membrane is still retained.

EXAMPLE 9

This example is an additional illustration that, unexpectedly, the immobilized biological membrane according to the present invention retains membrane function. As summarized herein, any attempt to immobilize a biological membrane could potentially affect the activity inherent to components of the membrane in its natural setting. In that regard, to be a particularly useful biological supported membrane, some specific biological activity of the biological membrane should be retained.

To further assess whether the methods of the present invention for producing an immobilized biological membrane also resulted in an immobilized biological membrane retaining some biological function, membrane protein-associated ion transport activity was measured. More specifically, and in continuing with the illustration of using an erythrocyte membrane complex as the biological membrane deposited onto an alkanethiol monolayer-coated substrate, cyclic voltammetry measurements were performed.

Figure 4:
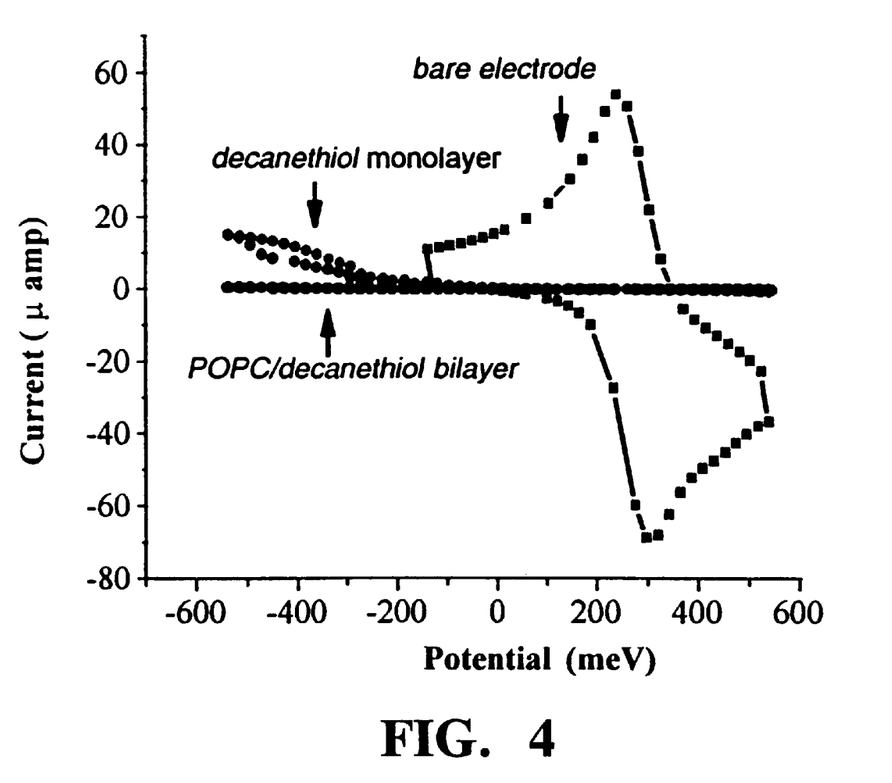
FIG. 4 is a graph illustrating the insulating properties of alkanethiol monolayers and alkanethiol monolayer/lipid bilayers as coatings on substrates.

Using the materials and methods according to Example 1 herein, the biological membrane was deposited onto an alkanethiol monolayer-coated substrate. Cyclic voltammetry was performed with $K_3Fe(CN)_6$, or with an equimolar mixture of $K_3Fe(CN)_6$ and $K_4Fe(CN)_6$, as the redox species in either 1M or 0.1M KCl as the supporting electrolyte (Plant et al., 1993, *Langmuir* 11:2764–2767). As shown in FIG. 4, the potential-dependent current response associated with electron transfer between a bilayer-modified gold electrode and a soluble redox species (potassium ferricyanide) is indicative of the insulating properties of alkanethiol monolayers and alkanethiol monolayer/lipid bilayers as coatings on substrates. Compared to a bare gold electrode (FIG. 4, -■-), an electrode covered with an alkanethiol monolayer exhibits significantly reduced current (FIG. 4, "decanethiol monolayer", "-●-"), and requires the application of increasingly negative potentials in order to produce sufficient driving force to reduce ferricyanide. The addition of a phospholipid layer to the alkanethiol monolayer increases this insulating effect (FIG. 4, "POPC/decanethiol monolayer", "-●-"). At a highly insulating electrode, such as alkanethiol monolayer/phospholipid bilayer hybrid, electron transfer does not appear to be diffusion dependent and exhibits no or little effect of concentration of redox species or scan rate on current or reduction potential.

Figure 5:
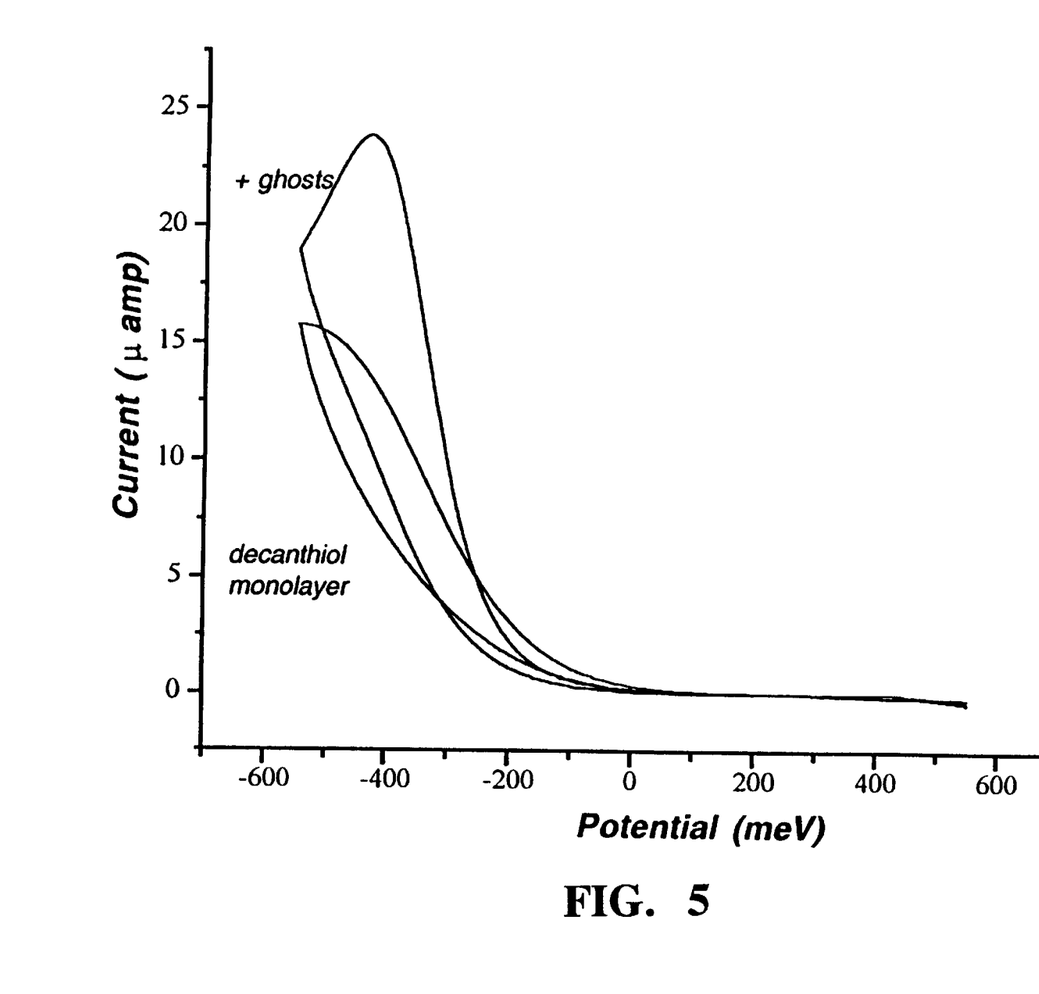
FIG. 5 is a graph illustrating the electron transfer of an immobilized biological membrane ("ghosts") as compared to an alkanethiol monolayer ("decanethiol monolayer").
Figure 6:
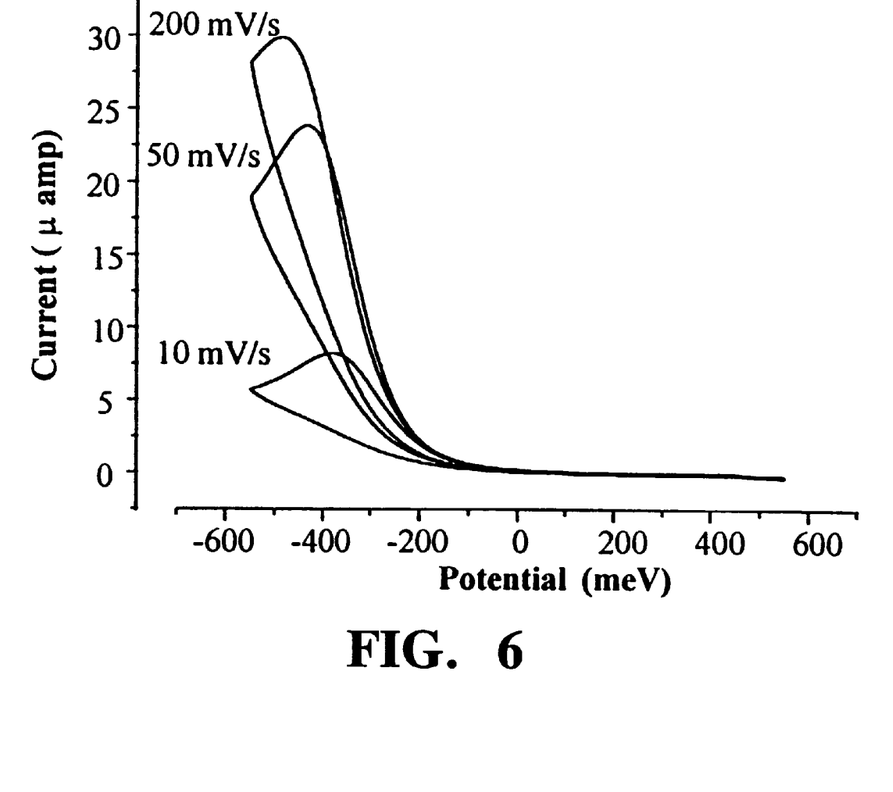
FIG. 6 is a graph illustrating that the immobilized biological membrane enables diffusion dependent electron transfer.
Figure 7:
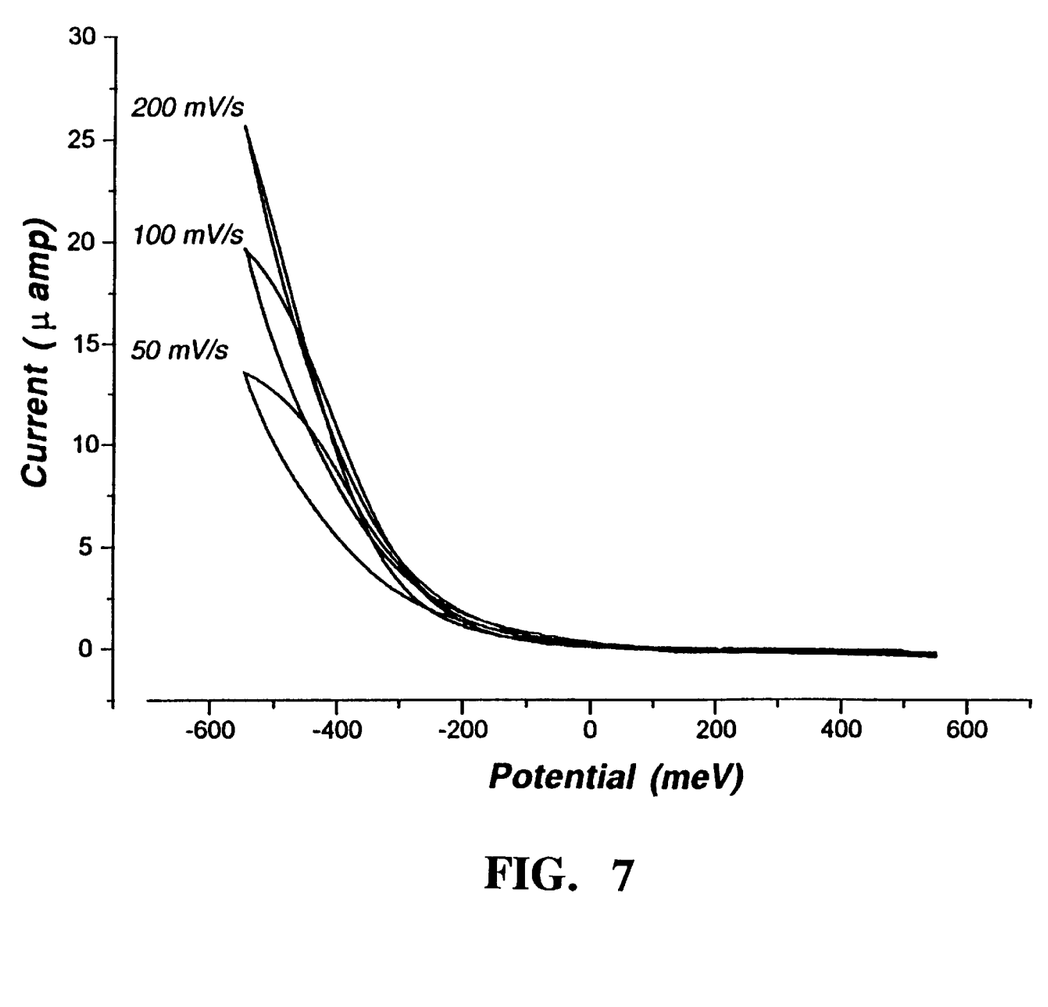
FIG. 7 is a graph illustrating treatment of the immobilized biological membrane with a potent inhibitor of anion transport mediated by a protein associated with the biological membrane.

However, and as illustrated in FIG. 5, an immobilized biological membrane (e.g., alkanethiol monolayer/erythrocyte membrane complex hybrid; FIG. 5, "ghosts") surface showed an increase in electron transfer as compared to an alkanethiol monolayer (FIG. 5, "decanethiol monolayer"), and observed was an appearance of electron transfer at a potential closer to its formal potential. As illustrated in FIG. 6, this redox response was also diffusion dependent as determined by altering the rate of potential scan. This response is an indication that the biological membrane layer at the surface enables the transfer of electrons between ferricyanide and the gold electrode by allowing the diffusion of ferricyanide towards the electrode surface. Illustrated in FIG. 7 is the treatment of the immobilized biological membrane with 2 mM DIDS, a potent inhibitor of anion transport mediated by an erythrocyte membrane protein ("Band 3" protein). After removing the DIDS solution and adding back ferricyanide, it is observed that electron transfer is significantly blocked again. The potential required for reduction shows less diffusion dependence compared to before DIDS addition. Thus, at least part of the electron transfer at an immobilized biological membrane is blocked by a compound which is known to block membrane protein-dependent anion transporter activity. In control experiments, DIDS was ineffective at blocking electron transfer at an electrode covered with a discontinuous alkanethiol monolayer.

FIGS. 6 and 7 illustrate that anion transport mediated by erythrocyte membrane proteins is clearly retained after the erythrocyte membrane complex is immobilized onto an alkanethiol monolayer-coated substrate. Thus, despite immobilization, the erythrocyte membrane complex still retained biological function of the membrane.

EXAMPLE 10

Illustrated in previous examples herein is the production of an immobilized and functional biological membrane formed by the deposition of cell membranes onto an alkanethiol monolayer, wherein the alkanethiol monolayer is assembled onto the metal of a support structure. It will be recognized that various modifications of these embodiments exist for preparing the immobilized biological membranes according to the present invention. For example, it is important to note that immobilization of the biological membrane onto the alkanethiol monolayer can be enhanced by any one of several methods known in the art for improving the association between two biological molecules. For example, the associative interaction between the deposited biological membrane and the alkanethiol monolayer may be enhanced by further promoting hydrophobic, electrostatic, or covalent interactions, or a combination thereof. It is appreciated that enhancing the associative interactions in producing an immobilized biological membrane will, of course, depend on the intended use of the resultant biological membrane. That is, each method of making the immobilized biological membrane will likely have certain advantages for particular usage applications. In that regard, while promoting covalent interactions may provide a supported biological membrane that is more resistant to destabilizing forces, lateral mobility of the membrane components in such immobilized biological membrane may be inhibited. On the other hand, where hydrophobic interactions are the primary associative interactions, the immobilized biological membrane may exhibit lateral mobility characteristic of biological membranes, but may suffer from reduced support (immobilized) life. To promote hydrophobic interactions in the associative interactions, alkanethiols used to form the alkanethiol monolayer may be chosen for functional groups which promote such hydrophobic interactions with the biological membrane (e.g., alkyl groups which couple to hydrophilic polymer/protein backbones). Alternatively, such functional groups may be added to the alkanethiol monolayer before deposition of the biological membrane. Further, using techniques known in the art, after such functional groups interact with the biological membrane, intramolecular crosslinking may be achieved by exposing the immobilized biological membrane to radiation. Similarly, there are reactive functional groups which promote covalent bonding, e.g., by the formation of ester, ether, or amide bonds. Such reactive functional groups may naturally comprise part of the alkanethiol, or may be added to the alkanethiol monolayer before deposition of the biological membrane. As the specific nature of such additional hydrophobic or covalent bonding is not critical to produce the invention, and does not in and of itself constitute the subject matter of the present invention, it should be apparent to those skilled in the art that a wide latitude of choice can be exercised in modifying the immobilized biological membrane according to the present invention.

EXAMPLE 11

This example illustrates a usage application of an immobilized biological membrane according to the present invention. More particularly, illustrated herein is a biosensor comprising an immobilized biological membrane according to the present invention. The biosensor has a configuration comprising an electrical insulating base/substrate provided with an electrode system including a plurality of electrodes; an electrolyte (solid phase or liquid phase, depending on the reactant to be measured); a processor means for performing test sequences to measure desired parameter values of the reactant to be detected; and the biological membrane immobilized on the surface of at least one of the electrodes, wherein the biological membrane has at least one component or activity for specifically interacting with or measuring of the reactant to be detected or measured, thereby functioning as a sensing indicator. The electrodes may include a working electrode, a counter-electrode and a reference electrode. The biosensor may further comprise a memory means for storing test sequences and/or measured parameter values. In operation, the biosensor is contacted with a sample suspected of containing the reactant to be detected, and then assayed is the level of activity associated with a specific interaction between the reactant and the immobilized biological membrane of the biosensor, thereby providing a sensitive measure of detection of the reactant, if present in the sample.

While erythrocyte membrane complex is used herein as a standard experimental model for other biological membranes, immobilized and functional erythrocyte membrane complex itself has commercial applications. For example, a biosensor may be fabricated using the immobilized erythrocyte membrane complex and its associated ACTHase activity as a sensing indicator. It is appreciated by those skilled in the art that there are several classes of inhibitors which are known to target ACTHase. Relevant to one commercial application, it is known that pesticide agents, particularly organophosphorus insecticides, are potent inhibitors of ACTHase (see, e.g., Yuknavage et al., 1997, *J. Toxicol. Environ. Health* 51:35–55; Parron et al., 1996, *Hum. Exp. Toxicol.* 15:957–63). Thus, contacting the biosensor with a sample suspected of containing organophosphorus insecticides and then assaying for the level of ACTHase activity associated with the biosensor in contact with the sample, may provide a sensitive measure of detection of exposure to these agents.

In another embodiment, cytotoxic agents useful in anti-cancer therapy have been shown to inhibit ACTHase activity associated with erythrocyte membranes (e.g., cisplatin: Kamal, 1996, *Anticancer Res.* 16:3725–30; methotrexate: Kamal et al., 1996, *Mol. Cell. Biochem.* 159:47–53). A biosensor may be fabricated using the immobilized erythrocyte membrane complex and its associated ACTHase activity as a sensing indicator, and contacted with a sample for determining the concentration of a cytotoxic drug in the sample (e.g., for monitoring drug treatment in a patient).

In yet another embodiment, pharmaceutical agents useful in the treatment of Alzheimer's disease have been shown to inhibit ACTHase activity associated with erythrocyte membranes (e.g., tacrine: Johansson, 1996, *Dementia* 7:111–17; eptastigmine: Canal and Imbimbo, 1996, *Clin. Pharmacol. Ther.* 60:218–28; donepezil: Rogers and Friedhoff, 1996, *Dementia* 7:293–303). A biosensor may be fabricated using the immobilized erythrocyte membrane complex and its associated ACTHase activity as a sensing indicator, and contacted with a sample for determining the concentration of the drug in the sample (e.g., for monitoring drug treatment in a patient being treated for Alzheimer's disease).

In a further embodiment, a biosensor may be fabricated for screening agents for desired pharmacologic activity. For example, ACTHase activity associated with erythrocyte membranes has been used for assessing free radical-induced damage (Hajela et al., 1997, supra) and the prevention thereof by antioxidants (Chan and Tang, 1996, supra; and Oya et al., 1997, supra). Thus, a biosensor may be fabricated using the immobilized erythrocyte membrane complex and its associated ACTHase activity as a sensing indicator, and contacted with a sample containing an agent to be assessed for antioxidant activity and in the presence of free-radicals.

As appreciated by those skilled in the art, depending on the intended use of the resultant immobilized biological membrane, certain cell types (and stages of differentiation) or cell organelles may be desirable from which to isolate the biological membrane. That is, the choice of the biological membrane to be deposited in making the immobilized biological membrane will likely have certain advantages for particular usage applications. For example, biosensors are used to detect the existence of microorganisms (e.g., bacteria, viruses, and parasites), chemical compounds in human body fluids (e.g., ions, glucose, LDL, antibodies, cytokines, immune effector cells), and other reactants present in the environment or in industrial settings. Thus, the biological membrane should contain at least one membrane component or activity suitable for use as a sensing indicator for the particular reactant(s) to be detected, and hence, the particular usage application.

EXAMPLE 12

This example illustrates other usage applications of an immobilized biological membrane according to the present invention. In one embodiment illustrated herein is a mechanically stable particulate support dimensioned for use in a chromatographic system and comprising an immobilized biological membrane according to the present invention. Thus, the surface of the support is coated with an alkanethiol monolayer/biological membrane hybrid. As known in the art of chromatography, such a mechanically stable particulate support can be of porous or nonporous material including, but not limited to, alumina, silica, metals, colloids, and polymers (including resins) having sufficient structural integrity to withstand the pressures characteristic of chromatography systems. Further, the particulate support may be of a size characteristic for chromatography systems, e.g. 5 to 100 microns in diameter.

The choice of the biological membrane to be deposited in making the immobilized biological membrane will likely have certain advantages for particular chromatographic applications. Thus, the biological membrane should contain at least one membrane component for use as an adsorbent to bind the specific reactant desired to be bound. For example, erythrocyte membrane complex from erythrocytes positive for A and B blood group antigens, can be used as the immobilized biological membrane in a chromatographic system to remove plasma anti-A or anti-B antibodies.

In another embodiment illustrated herein, provided is a medical device for implantation in an individual such as a human. For example, the medical device may comprise a vascular graft or prostheses which comprises a support material of flexible nature and structural integrity characteristic of vascular grafts, and an immobilized biological membrane according to the present invention. Such support material includes, but is not limited to, synthetic or polyester materials of sufficient weight, thickness, and bursting strength to function as a graft. The inner surface of the support is coated with an alkane (including, but not limited to, alkanethiol or alkylsilane) monolayer/biological membrane hybrid in forming an immobilized biological membrane. The biological membrane to be deposited, for making such an immobilized biological membrane, should be substantially nonimmunogenic and nonthrombogenic with respect to the recipient of the graft. For example, vascular endothelial cell membranes from allogeneic or autologous vascular endothelial cells may be used in forming the immobilized biological membrane.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. An immobilized biological membrane comprising:
    a support structure,
    a metal layered over a surface of the support structure,
    an alkanethiol monolayer deposited over the metal, and
    a biological membrane deposited over the alkanethiol monolayer,
    wherein the immobilized biological membrane retains at least a portion of natural membrane function or activity.

2. The immobilized biological membrane according to claim 1, wherein the biological membrane is deposited over the alkanethiol monolayer by vesicle spreading.

3. The immobilized biological membrane according to claim 1, wherein the biological membrane is deposited over the alkanethiol monolayer by Langmuir-Blodgett transfer.

4. The immobilized biological membrane according to claim 1, wherein the biological membrane comprises lipids, proteins and carbohydrate moieties.

5. The immobilized biological membrane according to claim 1, wherein the biological membrane and the alkanethiol monolayer interact via a means selected from the group consisting of hydrophobic interactions, covalent bonds, electrostatic interactions, intramolecular crosslinking, and a combination thereof.

6. The immobilized biological membrane according to claim 1, wherein the alkanethiol is selected from the group consisting of octadecanethiol, and decanethiol.

7. The immobilized biological membrane according to claim 1, wherein the metal is gold.

8. The immobilized biological membrane according to claim 1, wherein the support structure is selected from the group consisting of metal, glass, composite or synthetic polymer, carbon, and silicon.

9. A method of producing the immobilized biological membrane according to claim 1, comprising the steps of:
    (a) depositing a metal layer over the surface of a support structure;
    (b) contacting an alkanethiol with the metal layer to form an alkanethiol monolayer assembled over the metal; and
    (c) depositing a biological membrane over the alkanethiol monolayer.

10. The method according to claim 9, wherein the biological membrane is deposited over the alkanethiol monolayer by vesicle spreading.

11. The method according to claim 9, wherein the biological membrane is deposited over the alkanethiol monolayer by Langmuir-Blodgett transfer.

12. The method according to claim 1, wherein the biological membrane comprises lipids, proteins and carbohydrate moieties.

13. The method according to claim 9, wherein the alkanethiol is selected from the group consisting of octadecanethiol, and decanethiol.

14. The method according to claim 9, wherein the metal is gold.

15. The method according to claim 9, wherein the support structure is selected from the group consisting of metal, glass, composite or synthetic resin, carbon, and silicon.

16. A method of using the composition according to claim 1 to detect a reactant in a sample suspected of containing the reactant, said method comprises utilizing an immobilized biological membrane having at least one component or activity for specifically interacting with the reactant to be detected; contacting the immobilized biological membrane with the sample; and detecting the specific interaction between the immobilized biological membrane and the reactant if present in the sample.

17. A method of detecting a reactant in a sample suspected of containing the reactant, comprising the steps of:
    (a) contacting the immobilized biological membrane of claim with the sample, wherein the immobilized biological membrane has at least one component which reacts with the reactant to be detected; and (b) measuring a change in the activity of the component as an indicator of the presence or absence of the reactant.

18. A method of isolating a reactant in a sample comprising the steps of
   (a) contacting the immobilized biological membrane of claim 1 with the sample containing the reactant, wherein at least one component of the immobilized biological membrane specifically binds to the reactant;
   (b) removing the unbound materials; and
   (c) eluting the bound reactant.

* * * * *

UNITED STATES PATENT AND TRADEMARK OFFICE
CERTIFICATE OF CORRECTION

PATENT NO. : 5,919,576
DATED : July 6, 1999
INVENTOR(S) : Sek Wen Hui; Anne Plant; Madhusudhana Rao It is certified that error appears in the above-identified patent and that said Letters Patent is hereby corrected as shown below:

Col. 20, line 42 - "claim 1" should be --claim 9--

Col. 20, line 65 - after "claim" insert --1--

Signed and Sealed this

Eighteenth Day of January, 2000

Attest:

Q. TODD DICKINSON

*Attesting Officer*

*Commissioner of Patents and Trademarks*